US008542843B2

(12) United States Patent
Andrea et al.

(10) Patent No.: US 8,542,843 B2
(45) Date of Patent: Sep. 24, 2013

(54) HEADSET WITH INTEGRATED STEREO ARRAY MICROPHONE

(75) Inventors: Douglas Andrea, Sag Harbor, NY (US); Qunsheng Liu, Queens, NY (US); John Probst, Hauppauge, NY (US)

(73) Assignee: Andrea Electronics Corporation, Bohemia, NY (US)

( * ) Notice: Subject to any disclaimer, the term of this patent is extended or adjusted under 35 U.S.C. 154(b) by 400 days.

(21) Appl. No.: 12/429,623

(22) Filed: Apr. 24, 2009

(65) Prior Publication Data

US 2009/0268931 A1 Oct. 29, 2009

Related U.S. Application Data

(60) Provisional application No. 61/048,142, filed on Apr. 25, 2008.

(51) Int. Cl.
*A61F 11/06* (2006.01)
*G10K 11/16* (2006.01)
*H03B 29/00* (2006.01)

(52) U.S. Cl.
USPC ........ 381/71.11; 381/13; 381/71.1; 381/71.6; 381/71.7; 381/71.8

(58) Field of Classification Search
USPC .................. 381/71.1, 71.6, 71.7, 71.11, 71.8
See application file for complete search history.

(56) References Cited

U.S. PATENT DOCUMENTS

| | | | | |
|---|---|---|---|---|
| 5,815,582 | A * | 9/1998 | Claybaugh et al. | 381/71.6 |
| 5,825,897 | A | 10/1998 | Andrea et al. | |
| 6,118,878 | A | 9/2000 | Jones | |
| 6,430,295 | B1 | 8/2002 | Handel et al. | |
| 7,065,219 | B1 | 6/2006 | Abe et al. | |
| 7,092,529 | B2 * | 8/2006 | Yu et al. | 381/71.11 |
| 8,160,261 | B2 | 4/2012 | Schulein et al. | |
| 2005/0207585 | A1 | 9/2005 | Christoph | |
| 2006/0239471 | A1 | 10/2006 | Mao et al. | |
| 2006/0270468 | A1 * | 11/2006 | Hui et al. | 455/570 |
| 2007/0023851 | A1 | 2/2007 | Hartzell et al. | |
| 2007/0287380 | A1 | 12/2007 | Hui et al. | |
| 2008/0175408 | A1 | 7/2008 | Mukund et al. | |

FOREIGN PATENT DOCUMENTS

| | | |
|---|---|---|
| WO | WO 2006/028587 | 3/2006 |
| WO | WO 2008/146082 | 12/2008 |
| WO | WO 2008/157421 | 12/2008 |

* cited by examiner

*Primary Examiner* — S. V. Clark
*Assistant Examiner* — Jesse Y Miyoshi
(74) *Attorney, Agent, or Firm* — Vedder Price P.C.; Thomas J. Kowalski; Rebecca G. Rudich

(57) ABSTRACT

The invention relates to a noise canceling audio transmitting/ receiving device; a stereo headset with an integrated array of microphones utilizing an adaptive beam forming algorithm. The invention also relates to a method of using an adaptive beam forming algorithm that may be incorporated into a stereo headset. The sensor array used herein has adaptive filtering capabilities.

20 Claims, 11 Drawing Sheets

HEADSET WITH INTEGRATED STEREO ARRAY MICROPHONE

INCORPORATION BY REFERENCE

The present application claims the benefit of Provisional Application No. 61/048,142 filed Apr. 25, 2008. The present application also makes reference to U.S. patent application Ser. No. 12/332,959 filed on Dec. 11, 2008, which claims benefit Provisional Application No. 61/012,884. All of these applications are incorporated herein by reference.

Each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

Citation or identification of any document in this application is not an admission that such document is available as prior art to the present invention.

BACKGROUND OF THE INVENTION

1. Field of the Invention

The invention generally relates to noise canceling audio transmitting/receiving devices such as headsets with microphones, and particularly relates to stereo headsets integrated with an array of microphones for use in internet gaming.

2. Description of Prior Art

There is a proliferation of mainstream PC games that support voice communications. Team chat communication applications are used such as Ventrilo®. These communication applications are being used on networked computers, utilizing Voice over Internet Protocol (VOIP) technology. PC game players typically utilize PC headsets to communicate via the internet and the earphones help to immerse themselves in the game experience.

When gamers need to communicate with team partners or taunt their competitors, they typically use headsets with close talking boom microphones, for example as shown in FIG. 7. The boom microphone may have a noise cancellation microphone, so their voice is heard clearly and any annoying background noise is cancelled. In order for these types of microphones to operate properly, they need to be placed approximately one inch in front of the user's lips.

Gamers are, however, known to play for many hours without getting up from their computer terminal. During prolonged game sessions, the gamers like to eat and drink while playing for these long periods of time. If the gamer is not communicating via VoIP, he may move the boom microphone with his hand into an upright position to move it away from in front of his face. If the gamer wants to eat or drink, he would also need to use one hand to move the close talking microphone from in front of his mouth. Therefore if the gamer wants to be unencumbered from constantly moving the annoying close talking boom microphone and not to take his hands away from the critical game control devices, an alternative microphone solution would be desirable.

Accordingly, there is a need for a high fidelity far field noise canceling microphone that possesses good background noise cancellation and that can be used in any type of noisy environment, especially in environments where a lot of music and speech may be present as background noise (as in a game arena or internet café), and a microphone that does not need the user to have to deal with positioning the microphone from time to time. Therefore, an object of the present invention is to provide for a device that integrates both these features. A further object of the invention is to provide for a stereo headset with an integrated array of microphones utilizing an adaptive beam forming algorithm. This preferred embodiment is a new type of "boom free" headset, which improves the performance, convenience and comfort of a game player's experience by integrating the above discussed features.

SUMMARY OF THE INVENTION

The present invention relates to a noise canceling audio transmitting/receiving device; a stereo headset with an integrated array of microphones utilizing an adaptive beam forming algorithm. The invention also relates to a method of using an adaptive beam forming algorithm that can be incorporated into a stereo headset.

One embodiment of the present invention may be a noise canceling audio transmitting/receiving device which may comprise at least one audio outputting component, and at least one audio receiving component, wherein each of the receiving means may be directly mounted on a surface of a corresponding outputting means. The noise canceling audio transmitting/receiving device may be a stereo headset or a ear bud set. At least one audio outputting means may be a speaker, headphone, or an earphone, and at least one audio receiving means may be a microphone. The microphone may be a uni or omni-directional electret microphone, or a microelectromechanical systems (MEMS) microphone. The noise canceling audio transmitting/receiving device may also include a connecting means to connect to a computing device or an external device, and the noise canceling audio transmitting/receiving device may be connected to the computing device or the external device via a stereo speaker/microphone input or Bluetooth® or a USB external sound card device. The position of at least one audio receiving means may be adjustable with respect to a user's mouth.

For a better understanding of the invention, its operating advantages and specific objects attained by its uses, reference is made to the accompanying descriptive matter in which preferred, but non-limiting, embodiments of the invention are illustrated.

BRIEF DESCRIPTION OF THE DRAWINGS

The accompanying drawings, which are included to provide a further understanding of the invention, are incorporated in and constitute a part of this specification. The drawings presented herein illustrate different embodiments of the invention and together with the description serve to explain the principles of the invention. In the drawings.

DETAILED DESCRIPTION OF THE INVENTION

According to an embodiment of the present invention, a sensor array, receives signals from a source. The digitized output of the sensors may then transformed using a discrete Fourier transform (DFT).

The sensors of the sensor array preferably are microphones. In one embodiment the microphones are aligned on a particular axis. In the simplest embodiment the array comprises two microphones on a straight line axis. Normally, the array consists of an even number of sensors, with the sensors, according to one embodiment, at a fixed distance apart from each adjacent sensor. However, arrangements with sensors arranged along different axes or in different locations, with an even or odd number of sensors may be within the scope of the present invention.

According to an embodiment of the invention, the microphones generally are positioned horizontally and symmetrically with respect to a vertical axis. In such an arrangement there are two sets of microphones, one on each side of the vertical axis corresponding to two separate channels, a left and right channel, for example.

In one embodiment, the microphones are digital microphones such as uni or omni-directional electret microphones, or micro machined microelectromechanical systems (MEMS) microphones. The advantage of using the MEMS microphones is they have silicon circuitry that internally converts an audio signal into a digital signal without the need of an A/D converter, as other microphones would require. In any event, after the signals are digitized, according to an embodiment of the present invention, the signals travel through adjustable delay lines that act as input into a microprocessor or a digital signal processor (DSP). The delay lines are adjustable, such that a user may control the direction in which the sensors or microphones receive sound signals or audio signals from, generally referred to hereinafter as a 'beam.' In one embodiment, the delay lines are fed into the microprocessor of a computer. In such an embodiment, as well as others, there may be a graphical user interface (GUI) that provides feedback to a user. For example, the interface may tell the user how narrow the beam produced from the array, the direction of the beam, and how much sound it is picking up from a source. Based on input from a user of the electronic device containing the microphone array, the user may vary the delay lines that carry the output of the digitizer or digital microphone to the microprocessor or DSP.

Figure 1:
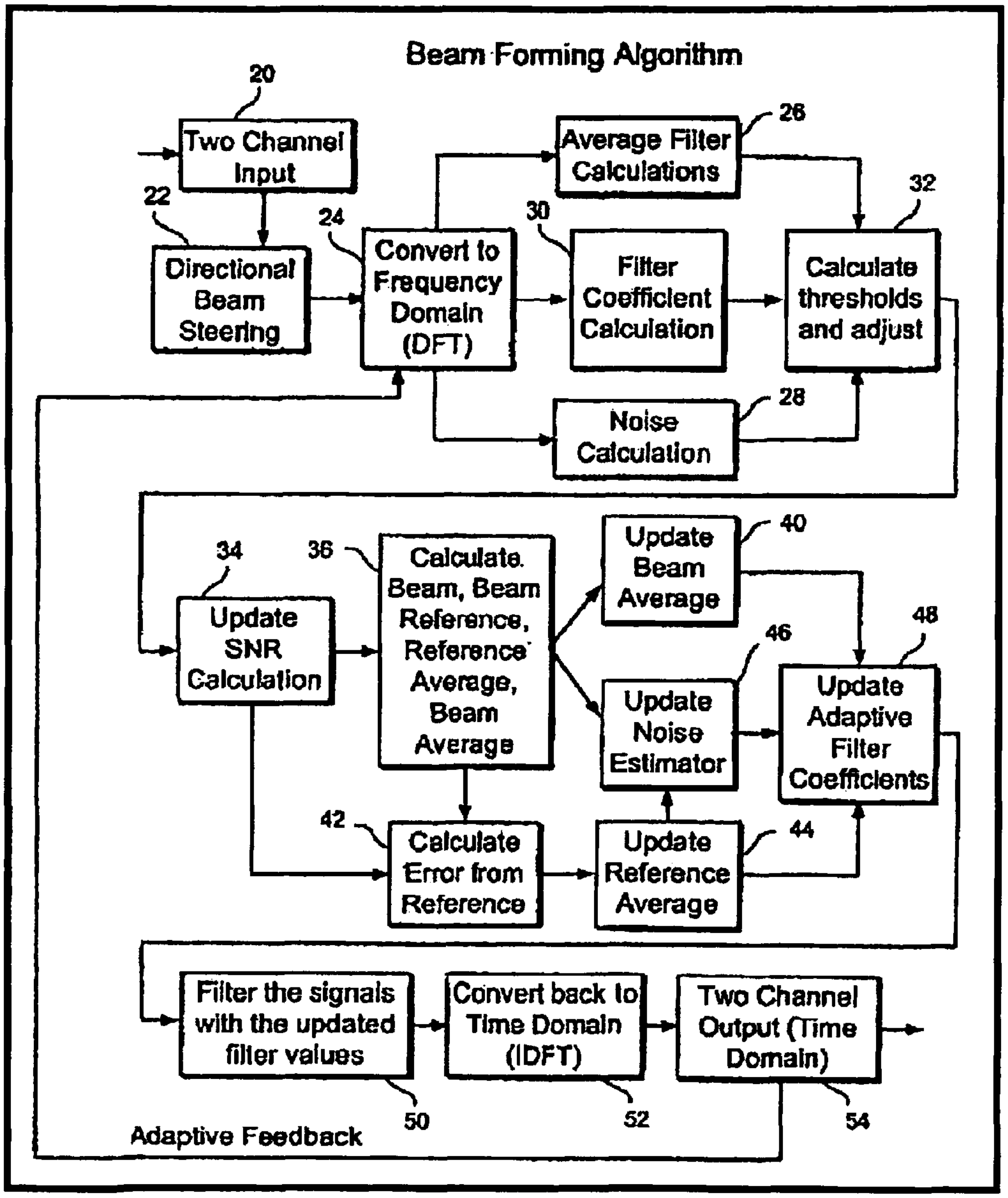
FIG. 1 is a schematic depicting a beam forming algorithm according to one embodiment of the invention.

The invention, according to one embodiment as presented in FIG. 1, produces substantial noise cancellation or reduction of background noise. After the steerable microphone array produces a two-channel input signal that may be digitized 20 and on which beam steering may be applied 22, the output may then be transformed using a DFT 24 to a frequency domain signal. It well known there are many algorithms that can perform a DFT. In particular a fast Fourier transform (FFT) may be used to efficiently transform the data so that it may be more amenable for digital processing. As mentioned before, the DFT processing may take place in a general microprocessor, or a DSP. After transformation, the data may be filtered according to the embodiment of FIG. 1.

This invention, in particular, applies an adaptive filter in order to efficiently filter out background noise. The adaptive filter may be a mathematical transfer function. The filter coefficients of such adaptive filters help determine the performance of the adaptive filters. In the embodiment presented, the filter coefficients may be dependent on the past and present digital input.

An embodiment as shown in FIG. 1 discloses an averaging filter that may be applied to the digitally transformed input 26 to smooth the digital input and remove high frequency artifacts. This may be done for each channel. In addition the noise from each channel may also determined 28. Once the noise is determined, different variables may be calculated to update the adaptive filter coefficients 30. The channels are averaged and compared against a calibration threshold 32. If the result falls below a threshold, the values are adjusted, by a weighting average function so as to reduce distortion by a phase mismatch between the channels.

Another parameter that may be calculated, according the embodiment in FIG. 1, is the signal to noise ratio (SNR). The SNR may be calculated from the averaging filter output and the noise calculated from each channel 34. The result of the SNR calculation, if it reaches a certain threshold, triggers modifying the digital input using the filter coefficients of the previously calculated beam. The threshold, which may be set by the manufacturer, may be a value in which the output may be sufficiently reliable for use in certain applications. In different situations or applications, a higher SNR may be desired, and the threshold may be adjusted by an individual.

The beam for each input may be continuously calculated. In an exemplary embodiment, a beam is the average of the two signals from the left and right channels, the average including the difference of angle between the target source and each of channels. Along with the beam, a beam reference, reference average, and beam average may also calculated 36. In this exemplary embodiment, the beam reference is a weighted average of a previously calculated beam and the adaptive filter coefficients, and a reference average is the weighted sum of the previously calculated beam references. In the exemplary embodiment, there may also be a calculation for beam average where the beam average is the running average of previously calculated beams. All these factors are used to update the adaptive filter.

Using the calculated beam and beam average, an error calculation may be performed by subtracting the current beam from the beam average 42. This error may then used in conjunction with an updated reference average 44 and updated beam average 40 in a noise estimation calculation 46. The noise calculation helps predict the noise from the system including the filter. The noise prediction calculation may be used in updating the coefficients of the adaptive filter 48 such as to minimize or eliminate potential noise.

After updating the filter and applying the digital input to it, the output of the filter may then be processed by an inverse discrete Fourier transform (IDFT). After the IDFT, the output then may be used in digital form as input into an audio application, such as, audio recording, VoIP, speech recognition in the same computer, or perhaps sent as input to another computing system for additional processing.

According to another embodiment, the digital output from the adaptive filter may be reconverted by a D/A converter into an analog signal and sent to an output device. In the case of an audio signal, the output from the filter may be sent as input to another computer or electronic device for processing. Or it may be sent to an acoustic device such as a speaker system, or headphones, for example.

The algorithm, as disclosed herein, may advantageously be able to produce an effective filtering of noise, including filtering of non-stationary or sudden noise such as a door slamming. Furthermore, the algorithm allows superior filtering, at lower frequencies while also allowing the microphone spacing small, such as little as 5 inches in a two element microphone embodiment. Previously microphones array would require substantially more amount of spacing, such as a foot or more to be able to have the same amount filtering at the lower frequencies.

Another advantage of the algorithm as presented is that it, for the most part, may require no customization for a wide range of different spacing between the elements in the array. The algorithm may be robust and flexible enough to automatically adjust and handle the spacing in a microphone array system to work in conjunction with common electronic or computer devices.

Figure 2:
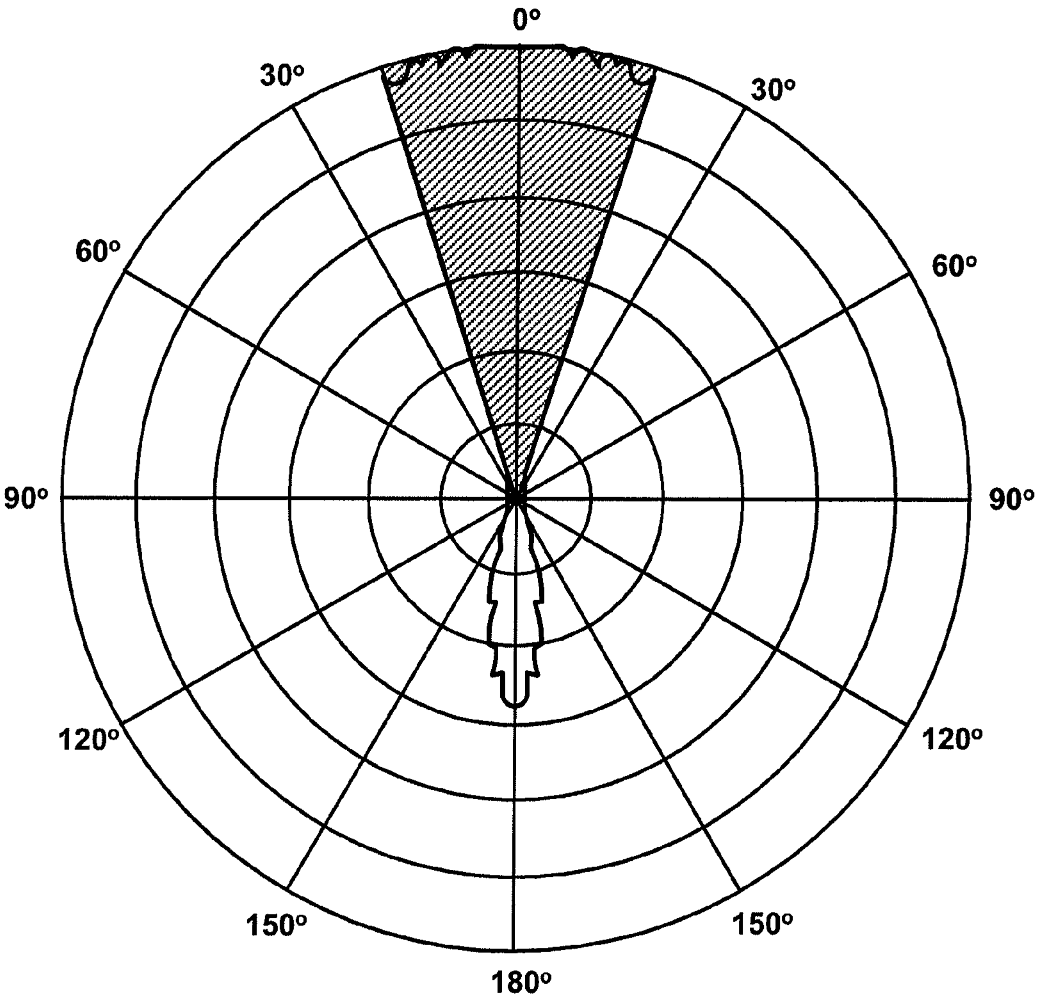
FIG. 2 is a drawing depicting a polar beam plot of a 2 member microphone array, according to one embodiment of the invention.

FIG. 2 shows a polar beam plot of a 2 member microphone array according to an embodiment of the invention when the delays lines of the left and right channels are equal. If the speakers are placed outside of the main beam, the array then attenuates signals originating from such sources which lie outside of the main beam, and the microphone array acts as an echo canceller with there being no feedback distortion. The beam typically will be focused narrowly on the target source, which is typically the human voice. When the target moves outside the beam width, the input of the microphone array shows a dramatic decrease in signal strength.

Figure 3:
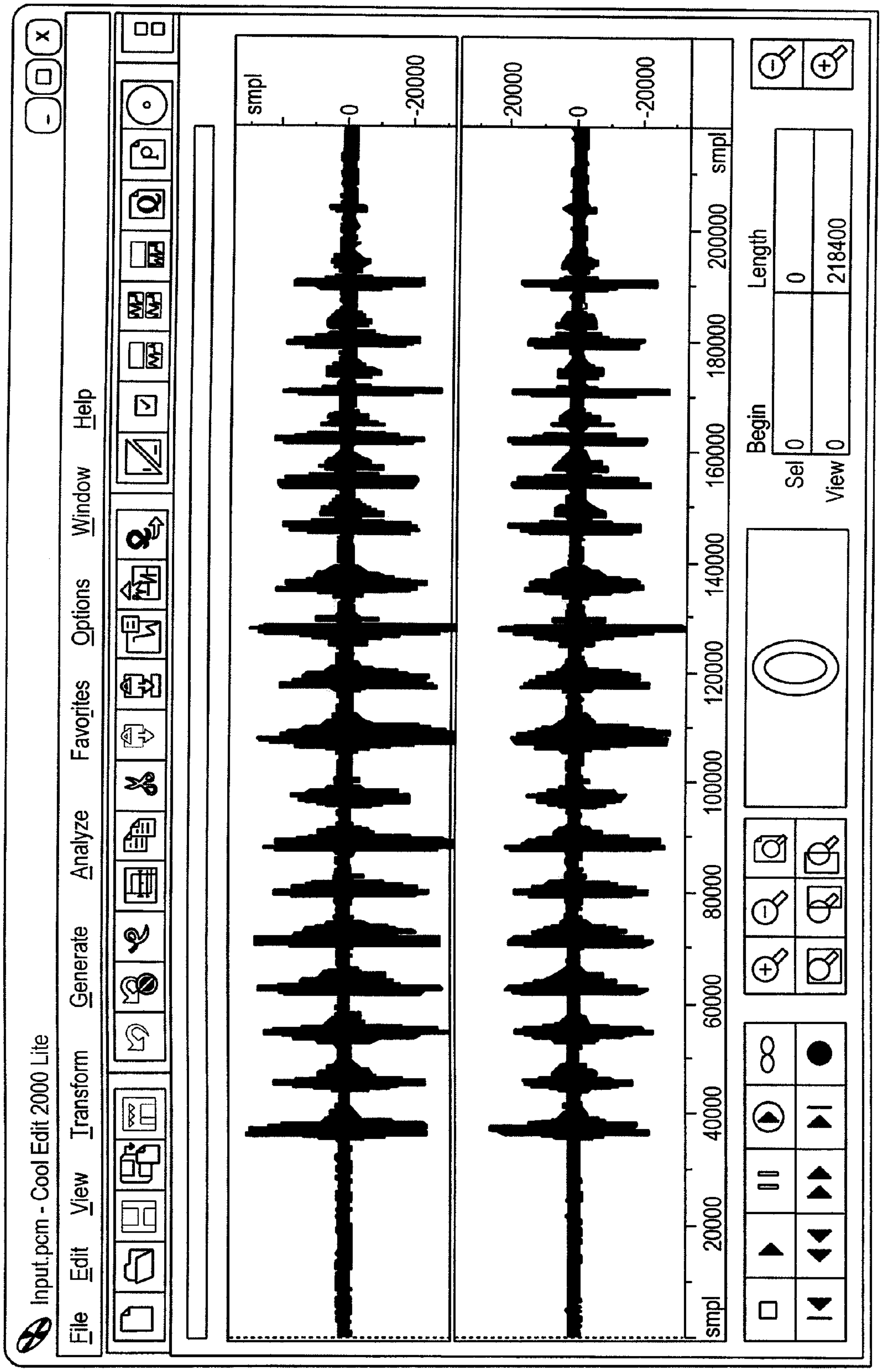
FIG. 3 shows an input wave file that is fed into a Microsoft® array filter and an array filter according to one embodiment of the present invention.

A research study comparing Microsoft®'s microphone array filters (embedded in the new Vista® operating system) and the microphone array filter according to the present invention is discussed herein. The comparison was made by making a stereo recording using the Andrea® Superbeam array. This recording was then processed by both the Microsoft® filters and the microphone array filter according to the present invention using the exact same input, as shown in FIG. 3. The recording consisted of:

1. A voice counting from 1 to 18, while moving in a 180 degree arc in front of the array.

2. A low level white noise generator was positioned at an angle of 45 degrees to the array.

3. The recording was at a sampling rate of 8000 Hz, 16-bit audio, which is the most common format used by VoIP applications.

For the Microsoft® filters test, their Beam Forming, Noise Suppression and Array Pre-Processing filters were turned on. For the instant filters test, the DSDA®R3 and PureAudio® filters were turned on, thus given the best comparison of the two systems.

Figure 4:
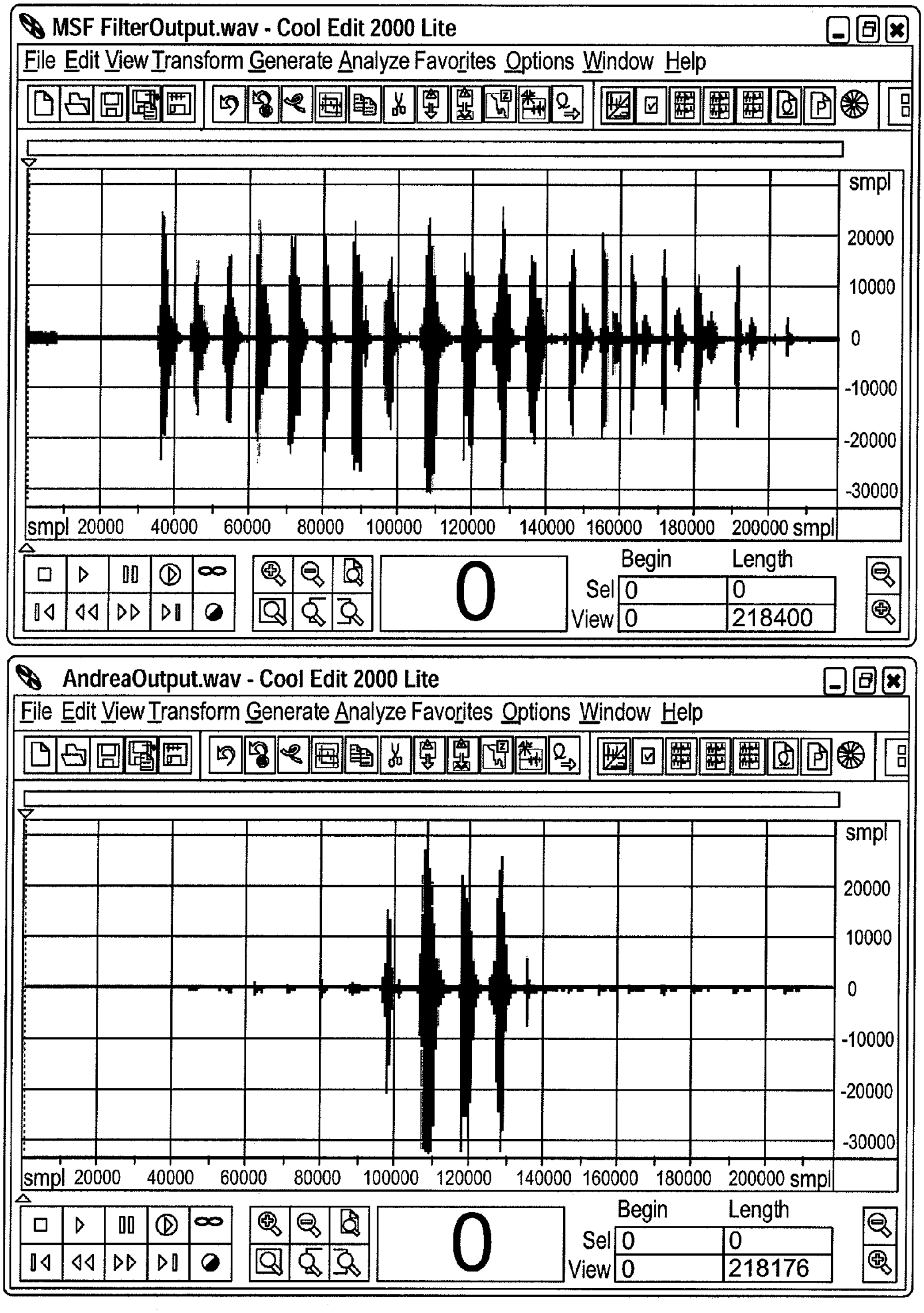
FIG. 4 depicts a comparison between the filtering of Microsoft® array filter with an array filter according to one embodiment of the present invention.

FIG. 4 shows the output wave files from both the filters. While the Microsoft® filters do improve the audio input quality, they use a loose beam forming algorithm. It was observed that it improves the overall voice quality, but it is not as effective as the instant filters, which are designed for environments where a user wants all sound coming from the side removed, such as voices or sound from multimedia speakers. The Microsoft® filters removed 14.9 dB of the stationary background noise (white noise), while the instant filters removed 28.6 dB of the stationary background noise. Also notable is that the instant beam forming filter has 29 dB more directional noise reduction of non-stationary noise (voice/music etc.) than the Microsoft® filters. The Microsoft® filters take a little more than a second before they start removing the stationary background noise. However, the instant filters start removing it immediately.

As shown in FIG. 4, the 12,000 mark on the axis represents when a target source or input source is directly in front of the microphone array. The 10,000 and 14,000 marks correspond to the outer parts of the beam as shown in FIG. 2. FIG. 4 shows, for example, a comparison between the filtering of Microsoft® array filter with an array filter disclosed according to an embodiment of the present invention. As soon as the target source falls outside of the beam width, or the 10,000 or 14,000 marks, there is very noticeably and dramatic roll off in signal strength in the microphone array using an embodiment of the present invention. By contrast, there is no such roll off found in Microsoft® array filter.

As someone in the art would recognize, the invention as disclosed, the sensor array could be placed on or integrated within different types of devices such as any devices that requires or may use an audio input, like a computer system, laptop, cellphone, gps, audio recorder, etc. For instance in a computer system embodiment, the microphone array may be integrated, wherein the signals from the microphones are carried through delay lines directly into the computer's microprocessor. The calculations performed for the algorithm described according to an embodiment described herein may take place in a microprocessor, such as an Intel® Pentium® or AMD® Athlon® Processor, typically used for personal computers. Alternatively the processing may be done by a digital signal processor (DSP). The microprocessor or DSP may be used to handle the user input to control the adjustable lines and the beam steering.

Alternatively in the computer system embodiment, the microphone array and possibly the delay lines may be connected, for example, to a USB input instead of being integrated with a computer system and connected directly to a microprocessor. In such an embodiment, the signals may then be routed to the microprocessor, or it may be routed to a separate DSP chip that may also be connected to the same or different computer system for digital processing. The microprocessor of the computer in such an embodiment could still run the GUI that allows the user to control the beam, but the DSP will perform the appropriate filtering of the signal according to an embodiment of an algorithm presented herein.

Figure 5:
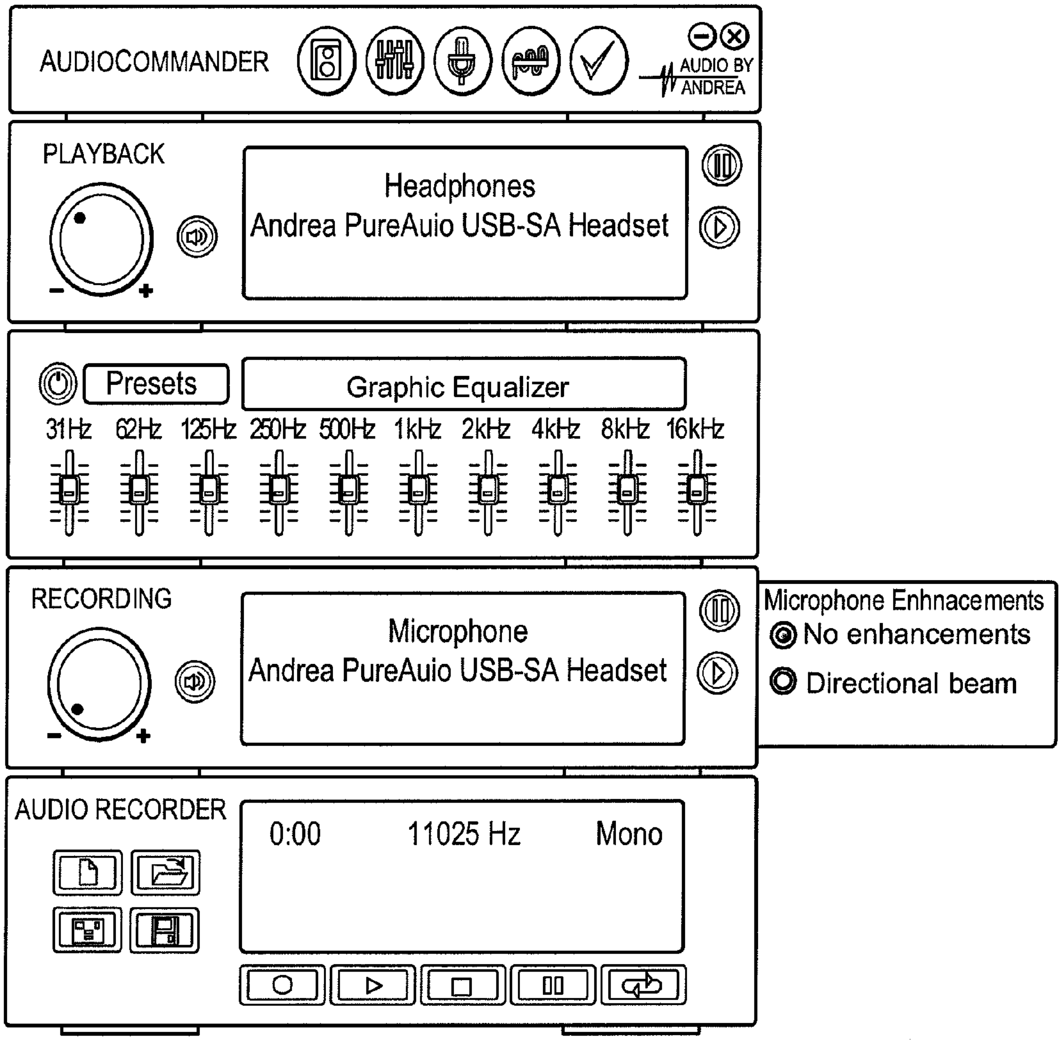
FIG. 5 is a depiction of an example of a visual interface that can be used in accordance with the present invention.
Figure 6:
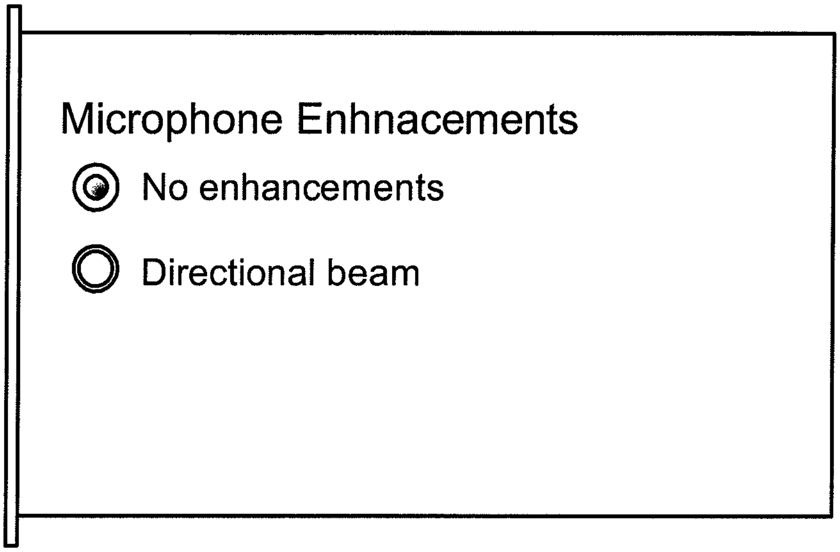
FIG. 6 is a portion of the visual interface shown in FIG. 5.
Figure 7:
FIG. 7 (PRIOR ART)
FIG. 7 is a photograph of a headset from prior art.

In some embodiments, the spacing of the microphones in the sensor array may be adjustable. By adjusting the spacing, the directivity and beam width of the sensor may be modified. FIGS. 5 and 6 show different aspects of embodiments of the microphone array and different visual user interfaces or GUIs that may be used with the invention as disclosed. FIG. 6 is a portion of the visual interface as shown in FIG. 5.

Figure 8:
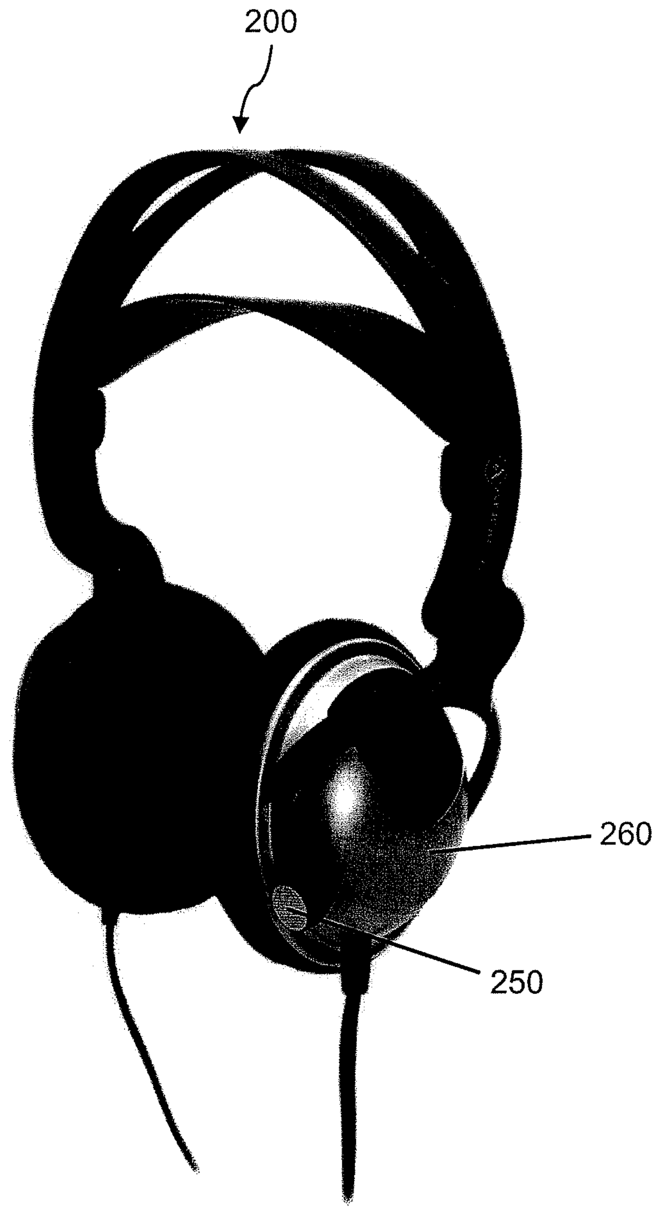
FIG. 8 is a photograph of a headset with microphones on either side, according to one embodiment of the invention.
Figure 9A:
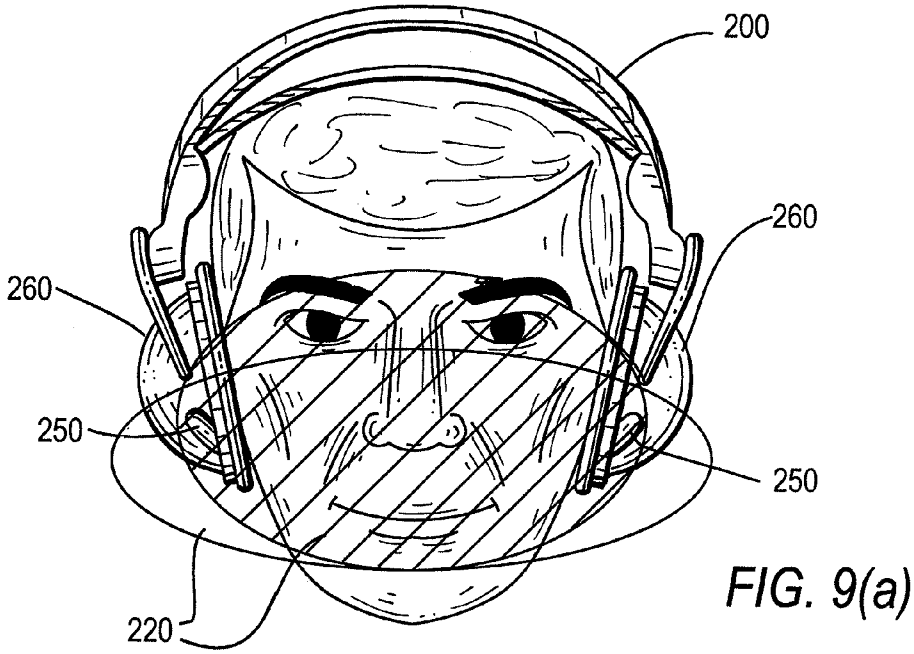
FIG. 9(*a*)-9(*d*) are illustrations of the headset, according to one embodiment of the invention.
Figure 9B:
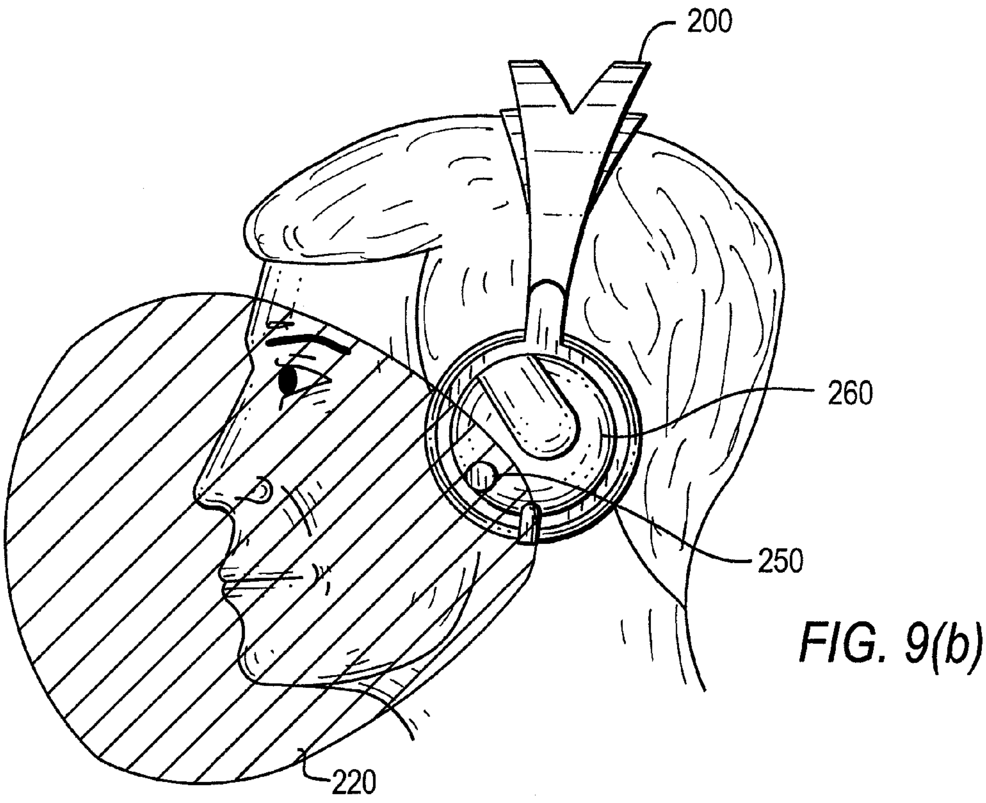
Figure 9C:
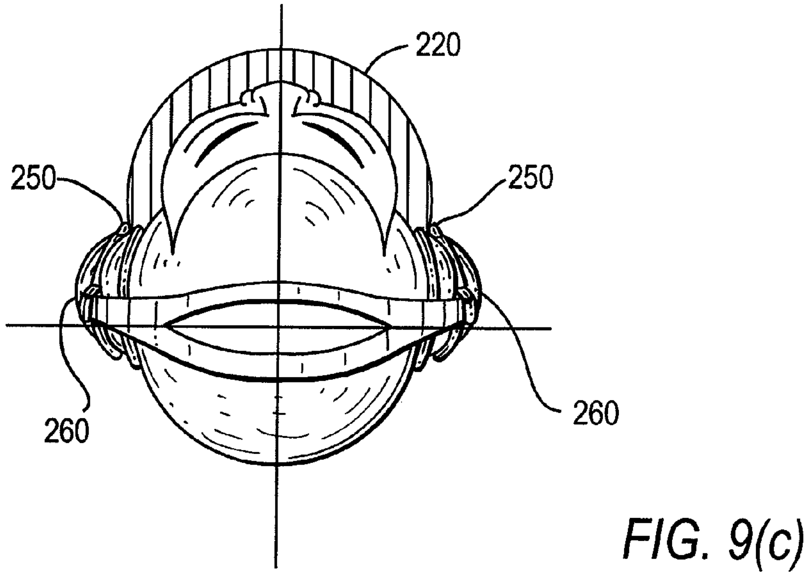
Figure 9D:
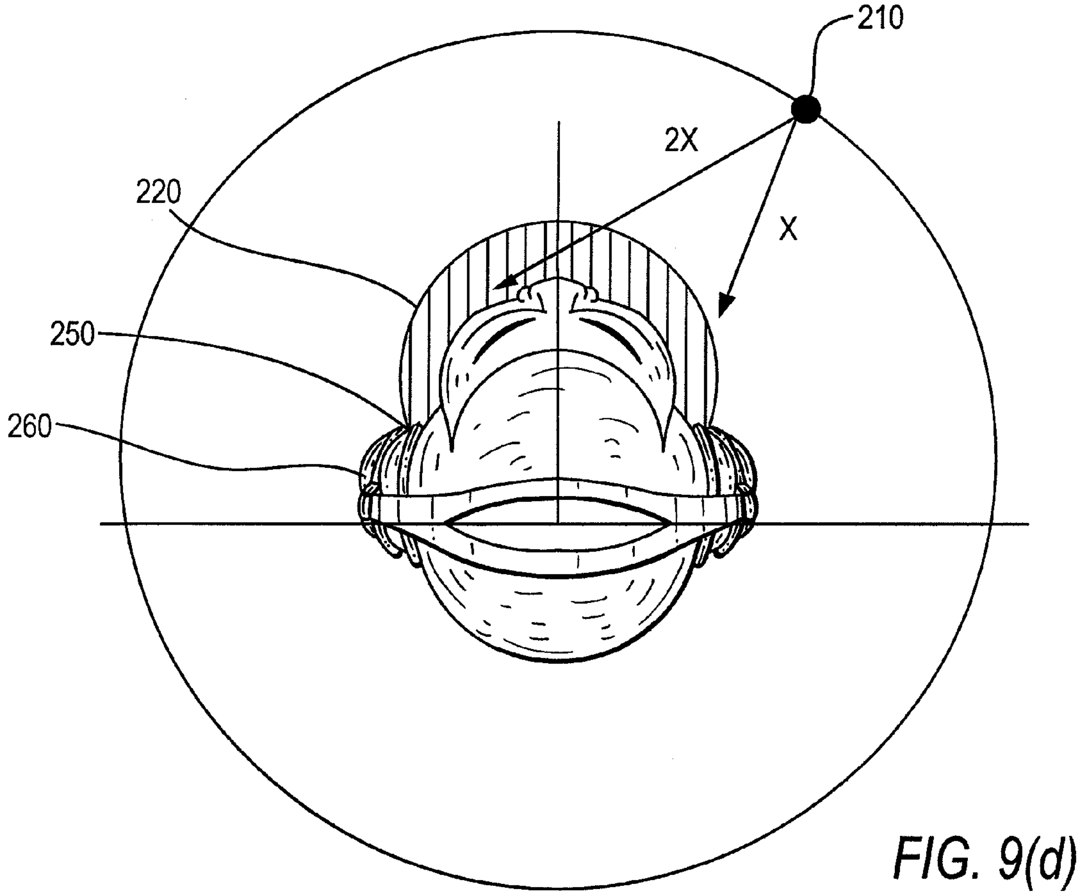

The invention according to a preferred embodiment may be an integrated headset system 200, a highly directional stereo array microphone with reception beam angle pointed forward from the ear phone to the corner of a user's mouth, as shown in FIG. 8. The pick-up angles or the angles in which the microphones 250 pick up sound from a sound source 210 is shown in FIG. 9(*d*), for example, in front of the array, while cancellation of all sounds occurs from side and back directions. Different views of this pick-up 'area' 220 are shown in FIGS. 9(*a*)-9(*c*). Cancellation is approximately 30 dB of noise, including speech noise.

According to this embodiment, left and right microphones 250 are mounted on the lower font surface of the earphone 260. They are, preferably, placed on the same horizontal axis. The user's head may be centered between the two earphones 260 and act as additional acoustic separation of the microphone elements 250. The spacing of microphones may range anywhere from 5 to 7 inches, for example.

By adjusting the microphone 250 spacing, the beam width may be adjusted. The closer the microphones are, the wider the beam becomes. The farther apart the microphones are, the narrower the beam becomes. It is found that approximately 7 inches achieves a more narrow focus on to the corner of the user's mouth, however, other distances are within the scope of the instant invention. Therefore, any acoustic signals outside of the array microphones forward pick up angle are effectively cancelled.

Figure 10:
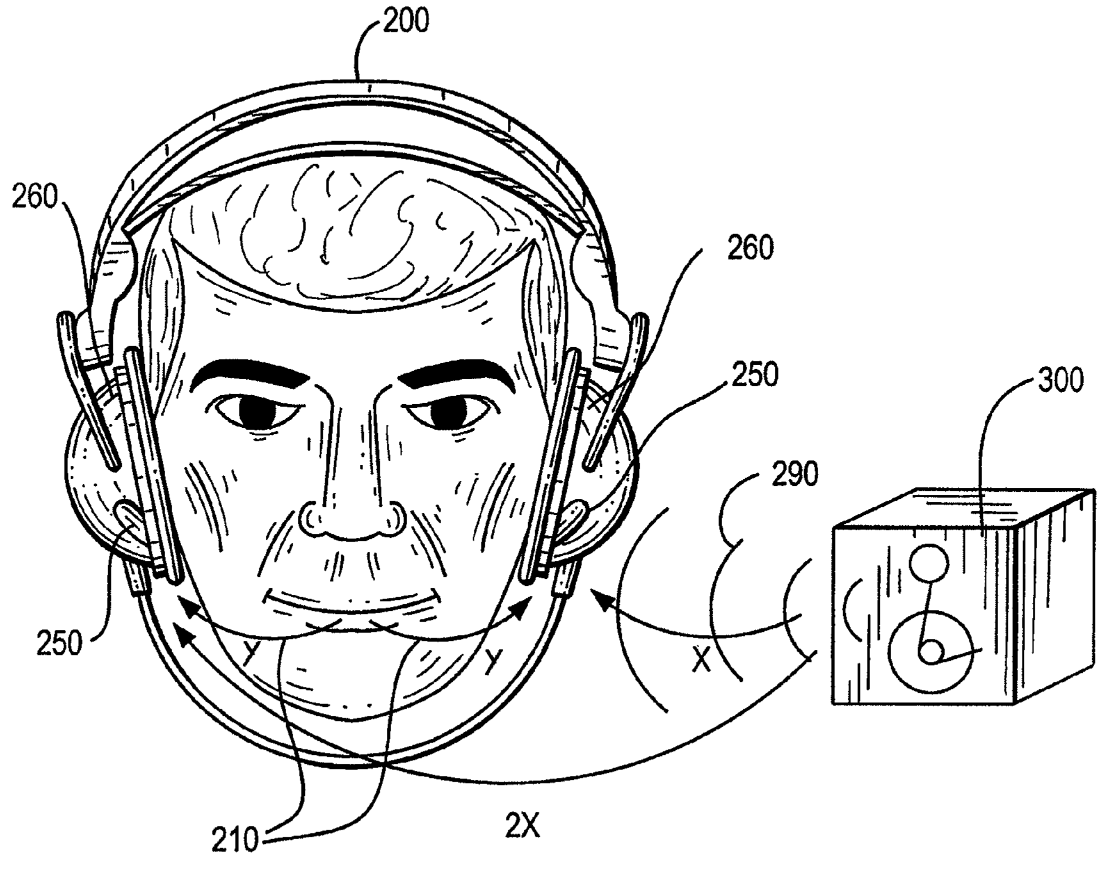
FIG. 10 is an illustration of the functioning of the headset with microphones, according to one embodiment of the invention.

The stereo microphone spacing allows for determining different time of arrival and direction of the acoustic signals to the microphones. From the centered position of the mouth, the voice signal 310 will look like a plain wave and arrive in-phase at same time with equal amplitude at both the microphones, while noise from the sides will arrive at each microphone in different phase/time and be cancelled by the adaptive processing of the algorithm. Illustration of such an instance is clearly shown in FIG. 10, for example, where noise coming from a speaker 300 on one side of the user is cancelled due to varying distances (X, 2X) of the sound waves 290 from either microphone 250. However, the voice signal 310 travels an equidistant (Y) to both microphones 250, thus providing for a high fidelity far field noise canceling microphone that possesses good background noise cancellation and that may be used in any type of noisy environment, especially in environments where a lot of music and speech may be present as background noise (as in a game arena or internet café).

The two elements or microphones 250 of the stereo headset-microphone array device may be mounted on the left and right earphones of any size/type of headphone. The microphones 250 may be protruding outwardly from the headphone, or may be adjustably mounted such that the tip of the microphone may be moved closer to a user's mouth, or the distance thereof may be optimized to improve the sensitivity and minimize gain. Acoustic separation may be considered between the microphones and the output of the earphones, as not to allow the microphones to pick up much of the received playback audio (known as crosstalk or acoustic feedback). Any type of microphone may be used, such as for example, uni-directional or omni-directional microphones.

The above described embodiment may be inexpensively deployed because most of today's PCs have integrated audio systems with stereo microphone input or utilize Bluetooth® or a USB external sound card device. Behind the microphone input connector may be an analog to digital converter (A/D Codec), which digitizes the left and right acoustic microphone signals. The digitized signals are then sent over the data bus and processed by the audio filter driver and algorithm by the integrated host processor. The algorithm used herein may be the same adaptive beam forming algorithm as described in the previous embodiments of the invention. Once the noise component of the audio data is removed, clean audio/voice may then be sent to the preferred voice application for transmission.

This type of processing may be applied to a stereo array microphone system that may typically be placed on a PC monitor with distance of approximately 12-18 inches away from the user's the mouth. In the present invention, however, the same array system may be placed on the persons head to reduce the microphone sensitivity and points the two microphones in the direction of the person's mouth.

Although the embodiments described herein relate to a stereo headset, the scope of the invention is not limited thereto. The invention may be integrated into smaller devices such as an ear bud, for example. The figures used herein are purely exemplary and are strictly provided to enable a better understanding of the invention. Accordingly, the present invention is not confined only to product designs illustrated therein.

Accordingly, one embodiment of the present invention may be a noise canceling audio transmitting/receiving device comprising at least one audio outputting component, and at least one audio receiving component, wherein each of the receiving means may be directly mounted on a surface of a corresponding outputting means. The noise canceling audio transmitting/receiving device may be a stereo headset or a ear bud set. At least one audio outputting means may be a speaker, headphone, or an earphone, and at least one audio receiving means may be a microphone. The microphone may be a uni or omni-directional electret microphone, or a microelectromechanical systems (MEMS) microphone. The noise canceling audio transmitting/receiving device may also include a connecting means to connect to a computing device or an external device, and the noise canceling audio transmitting/receiving device may be connected to the computing device or the external device via a stereo speaker/microphone input or Bluetooth® or a USB external sound card device. The position of at least one audio receiving means may be adjustable with respect to a user's mouth.

Thus by the present invention its objects and advantages are realized and although preferred embodiments have been disclosed and described in detail herein, its scope should not be limited thereby rather its scope should be determined by that of the appended claims.

The invention claimed is:

1. A noise canceling audio transmitting/receiving device, said device comprising:

at least one audio outputting means; and at least one audio receiving means, each for receiving an acoustic signal and outputting an electrical signal representing the received acoustic signal;

wherein each of said receiving means is directly mounted on a surface of a corresponding outputting means; and processing means connected to the audio receiving means and operable to apply a frequency domain adaptive filter to the electrical signal output by the audio receiving means, said processing means operable to carry out processing comprising:

applying an averaging filter on the digitized electrical signal output by each of the receiving means, continuously calculating a beam, a beam reference, a reference average, and noise estimation based on the output of the averaging filter to continuously update filter coefficients of the adaptive filter, and selectively applying the adaptive filter to the output of the averaging filter.

2. The device according to claim 1, wherein said noise canceling audio transmitting/receiving device is a stereo headset.

3. The device according to claim 2, wherein said at least one audio outputting means is a speaker, headphone, or an earphone.

4. The device according to claim 2, wherein said at least one audio receiving means is a microphone.

5. The device according to claim 4, wherein said microphone is a uni or omni-directional electret microphone, or a microelectromechanical systems (MEMS) microphone.

6. The device according to claim 1, wherein said noise canceling audio transmitting/receiving device further comprises a connecting means to connect to a computing device or an external device.

7. The device according to claim 6, wherein said noise canceling audio transmitting/receiving device can be connected to said computing device or said external device via a stereo speaker/microphone input or Bluetooth® or a USB external sound card device.

8. The device according to claim 1, wherein a position of said at least one audio receiving means is adjustable with respect to a user's mouth.

9. The device according to claim 1, wherein the audio receiving means comprises at least two audio receiving means.

10. The device according to claim 1, wherein each of at least two audio receiving means corresponds to a separate channel.

11. The device according claim 10, where a first one of said separate channels is a left channel and a second one of said separate channels is a right channel.

12. The device according to claim 10, wherein said processing performed by said processing means is performed for each separate channel.

13. The device according to claim 12, wherein said processing means further calculates a beam average representing an average of beams representing each of representing the acoustic signals on each of said separate channels, wherein said beam average is compared against threshold value and said filter coefficients are adjusted if said beam average is below said threshold.

14. The device according to claim 1, wherein the beam reference is an in-phase beam reference.

15. A noise canceling audio transmitting/receiving device, said device comprising:

at least one audio outputting means; and at least one audio receiving means, each for receiving an acoustic signal and outputting an electrical signal representing the received acoustic signal;

wherein each of the at least one audio receiving means is directly mounted on a surface of a corresponding outputting means; and processing means connected to the audio receiving means and configured to convert the electrical signal representing the received acoustic signal to a frequency domain signal, said processing means further configured to carry out processing comprising:

applying an averaging filter to the frequency domain signal by each of the at least one audio receiving means, repeatedly calculating a beam, a beam reference, a reference average, and noise estimation based on the output of the averaging filter to repeatedly update filter coefficients of a frequency domain adaptive filter, and applying the frequency domain adaptive filter to the output of the averaging filter; and calculating an error by subtracting the beam from a beam average, wherein calculating the noise estimation is further based on the error.

16. The device according to claim 15, wherein the beam average comprises an average of all previously calculated beams.

17. A noise canceling audio transmitting/receiving device, said device comprising:

at least one speaker; and at least two microphones each located a predetermined distance from an acoustic source and configured to output an electrical signal on a respective channel;

wherein each of the at least two microphones is mounted on a surface of a corresponding speaker; and a signal processor configured to receive from the microphones the electrical signals on each respective channel and to convert the time domain electrical signals to frequency domain electrical signals, said signal processor configured to apply an averaging filter to the frequency domain electrical signals, the signal processor further configured to calculate current filter coefficients for a beam representing the acoustic signal for application in said frequency domain adaptive filter, and to calculate a beam reference, a reference average, and a noise estimation based on output of the averaging filter to update filter coefficients of a frequency domain adaptive filter, and to apply the frequency domain adaptive filter to the output of the averaging filter;

wherein the signal processor is further configured to calculate an error by subtracting the beam from a beam average, wherein calculating the noise estimation is further based on the error.

18. The device according to claim 17, wherein the beam average comprises an average of all previously calculated beams.

19. The device according to claim 17, wherein each of said microphones is a highly directional microphone.

20. The device according to claim 17, wherein a position of each of said microphones is adjustable with respect the acoustic source.

* * * * *